(12) United States Patent
Theyson (10) Patent No.: US 9,737,474 B2
(45) Date of Patent: Aug. 22, 2017

(54) HAIR CONDITIONING COMPOSITIONS

(71) Applicant: Thomas W. Theyson, Matthews, NC (US)

(72) Inventor: Thomas W. Theyson, Matthews, NC (US)

(73) Assignee: TensTech, Inc., Matthews, NC (US)

( * ) Notice: Subject to any disclaimer, the term of this patent is extended or adjusted under 35 U.S.C. 154(b) by 0 days.

(21) Appl. No.: 14/774,322

(22) PCT Filed: Mar. 13, 2014

(86) PCT No.: PCT/US2014/025817
§ 371 (c)(1),
(2) Date: Sep. 10, 2015

(87) PCT Pub. No.: WO2014/160101
PCT Pub. Date: Oct. 2, 2014

(65) Prior Publication Data
US 2016/0030329 A1    Feb. 4, 2016

Related U.S. Application Data

(60) Provisional application No. 61/781,283, filed on Mar. 14, 2013.

(51) Int. Cl.
| *A61Q 5/00* | (2006.01) |
| *A61K 8/90* | (2006.01) |
| *A61Q 5/12* | (2006.01) |
| *A61Q 5/06* | (2006.01) |

(52) U.S. Cl.
CPC ............... *A61K 8/90* (2013.01); *A61Q 5/12* (2013.01); *A61Q 5/06* (2013.01)

(58) Field of Classification Search
None
See application file for complete search history.

(56) References Cited

U.S. PATENT DOCUMENTS

| 5,641,480 A | 6/1997 | Vermeer |
| 2011/0217255 A1* | 9/2011 | Kim ................. A61Q 5/06 424/70.11 |

FOREIGN PATENT DOCUMENTS

| WO | 9733556 A1 | 9/1997 |
| WO | 2012015069 A1 | 2/2012 |

OTHER PUBLICATIONS

Notification of Transmittal of the International Search Report and the Written Opinion for corresponding PCT Application No. PCT/US2014/025817, mailed Oct. 10, 2014, 7 pages.

* cited by examiner

*Primary Examiner* — Susan Tran
(74) *Attorney, Agent, or Firm* — Smith Moore Leatherwood LLP; John P. Zimmer (57) ABSTRACT

In one aspect, hair conditioning compositions are described herein. In some embodiments, a hair conditioning composition comprises a polymer or oligomer comprising (A) at least one hydrophilic block comprising an alkoxylated diol or amine-terminated derivative thereof and (B) at least one hydrophobic block comprising a condensation reaction product of (i) a dicarboxylic acid or dicarboxylic acid equivalent and (ii) a diamine, amino alcohol, diol, or combination thereof. The hydrophilic block (A) and the hydrophobic block (B) are bonded together through an amide or ester linkage. In addition, the polymer or oligomer comprises at least one amide moiety.

20 Claims, 5 Drawing Sheets

HAIR CONDITIONING COMPOSITIONS

CROSS REFERENCE TO RELATED APPLICATION APPLICATIONS

This application is a U.S. national stage application under 35 U.S.C. §371 of International Application No. PCT/US2014/025817 filed Mar. 13, 2014, which claims priority pursuant to 35 U.S.C. §119(e) to U.S. Provisional Patent Application Ser. No. 61/781,283, filed on Mar. 14, 2013, each of which is hereby incorporated by reference in its entirety.

FIELD

The present invention is related to hair conditioning compositions and, in particular, to hair conditioning compositions comprising polymers or oligomers.

BACKGROUND

Hair shampoos contain a variety of surface active agents designed to remove oil and dirt from hair. However, the use of shampoo alone can leave hair undesirably harsh, dull, and dry. In addition, shampooed hair can exhibit an increased tendency to tangle, which makes combing, brushing and styling of the hair difficult and even physically damaging to the hair. Furthermore, shampooed hair tends to produce static charge during brushing and combing, particularly in low humidity environments. The accumulation of static charge on hair can make the hair difficult to style and give the hair a "fly away" appearance.

To improve the properties of shampooed hair, many consumers apply a rinse off conditioner to their hair after shampooing. The use of a hair conditioner can reduce tangling and make hair easier to comb or brush, provide a softer feel to hair, and reduce the buildup of static charge to control "fly away" behavior.

There is a continuing need for improved hair conditioner compositions, particularly for hair conditioners that provide a high level of performance at low cost.

SUMMARY

In one aspect, hair conditioning compositions are described herein which, in some embodiments, may offer one or more advantages over prior hair conditioning compositions. In some embodiments, for example, a hair conditioning composition described herein provides a high level of hair conditioning functionality, including desirable wet comb, dry comb and/or static control properties. A hair conditioning composition described herein also, in some embodiments, exhibits one or more additional desirable properties, such as nonionic or anionic charge, the absence of silicone based components, and modest cost.

In some embodiments, a hair conditioning composition comprises a polymer or oligomer comprising (A) at least one hydrophilic block comprising an alkoxylated diol or amine-terminated derivative thereof and (B) at least one hydrophobic block comprising a condensation reaction product of (i) a dicarboxylic acid or dicarboxylic acid equivalent and (ii) a diamine, amino alcohol, diol, or combination thereof. The hydrophilic block (A) and the hydrophobic block (B) are bonded together through an amide or ester linkage. In addition, the polymer or oligomer comprises at least one amide moiety. In some embodiments described herein, the polymer or oligomer comprises a plurality of hydrophilic blocks connected by one or more hydrophobic blocks. In addition, in some embodiments, the polymer or oligomer comprises at least one anionic moiety.

Moreover, in some embodiments, the at least one hydrophilic block of a polymer or oligomer described herein has a molecular weight of at least about 1000 and is present in the polymer or oligomer in an amount of about 50 to about 90 weight percent, based on the total weight of the polymer or oligomer. The at least one hydrophobic block, in some embodiments, is present in the polymer or oligomer in an amount no greater than about 50 weight percent. Further, in some embodiments, the polymer or oligomer comprises a statistical copolymer or oligomer or a random copolymer or oligomer.

In addition, in some embodiments, a polymer or oligomer of a composition described herein has a weight average molecular weight between about 2000 and about 4500. In some embodiments, a polymer or oligomer is water dispersible.

These and other embodiments are described in greater detail in the detailed description which follows.

DETAILED DESCRIPTION

Embodiments described herein can be understood more readily by reference to the following detailed description, examples, and drawings. Elements, apparatus and methods described herein, however, are not limited to the specific embodiments presented in the detailed description, examples, and drawings. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" should generally be considered to include the end points 5 and 10.

In one aspect, hair conditioning compositions are described herein. In some embodiments, a hair conditioning composition comprises a polymer or oligomer comprising (A) at least one hydrophilic block comprising an alkoxylated diol or amine-terminated derivative thereof and (B) at least one hydrophobic block comprising a condensation reaction product of (i) a dicarboxylic acid or dicarboxylic acid equivalent and (ii) a diamine, amino alcohol, diol, or combination thereof. The hydrophilic block (A) and the hydrophobic block (B) are bonded together through an amide or ester linkage. In addition, the polymer or oligomer comprises at least one amide moiety. In some embodiments described herein, the polymer or oligomer comprises a plurality of hydrophilic blocks connected by one or more hydrophobic blocks. In addition, in some embodiments, the polymer or oligomer comprises at least one anionic moiety.

Turning now to specific components of hair conditioning compositions, a polymer or oligomer of a hair conditioning composition described herein comprises at least one hydrophilic block. In some embodiments, a polymer or oligomer comprises a plurality of hydrophilic blocks. A polymer or oligomer, in some embodiments, for example, comprises two hydrophilic blocks. In other embodiments, a polymer or oligomer comprises three hydrophilic blocks.

The hydrophilic block or blocks of a polymer or oligomer described herein can constitute any amount of the polymer or oligomer not inconsistent with the objectives of the present invention. In some embodiments, for instance, the hydrophilic blocks are present in the polymer or oligomer in an amount of about 50 weight percent to about 90 weight percent, based on the total weight of the polymer of oligomer. In some embodiments, the hydrophilic blocks are present in the polymer or oligomer in an amount of about 50 weight percent to about 80 weight percent, about 60 weight percent to about 90 weight percent, about 60 weight percent to about 80 weight percent, about 60 weight percent to about 75 weight percent, or about 65 weight percent to about 85 weight percent. In some embodiments, the hydrophilic blocks are present in the polymer or oligomer in an amount of about 70 weight percent to about 80 weight percent.

In addition, an individual hydrophilic block can have any molecular weight or average molecular weight not inconsistent with the objectives of the present invention. In some embodiments, for instance, a hydrophilic block has a molecular weight or weight average molecular weight of at least about 1000. In some embodiments, a hydrophilic block has a molecular weight or weight average molecular weight of at least about 1400 or at least about 2000. In some embodiments, a hydrophilic block has a molecular weight or weight average molecular weight between about 1000 and about 10,000, between about 1400 and about 4500, between about 1400 and about 3000, or between about 1400 and about 2000. In some embodiments, a hydrophilic block has a molecular weight or weight average molecular weight between about 2000 and about 3000.

A hydrophilic block of a polymer or oligomer described herein comprises an alkoxylated diol or amine-terminated derivative thereof. Any alkoxylated diol not inconsistent with the objectives of the present invention may be used. For example, in some embodiments, an alkoxylated diol comprises a polyoxyalkylene glycol such as poly(ethylene glycol), polypropylene glycol), or poly(butylene glycol). Further, an amine-terminated derivative of an alkoxylated diol, in some embodiments, comprises an alkoxylated diol modified to include an amino group at one or more terminal positions.

An alkoxylated diol can be obtained in any manner not inconsistent with the objectives of the present invention. In some embodiments, for instance, an alkoxylated diol is prepared by the reaction of a diol and ethylene oxide, propylene oxide, butylene oxide, or a mixture thereof. Useful diols, in some embodiments, comprise one or more of ethylene glycol, 1,2-propylene glycol, diethylene glycol, dipropylene glycol, triethylene glycol, tripropylene glycol, tetraethylene glycol, 1,3-propanediol, 1,4-butanediol, 1,6-hexanediol, 2-methylpentane-2,4-diol (hexylene glycol), 2,2,4-trimethylpentane-1,3-diol (sold under the trade name TEXANOL), neopentyl glycol or related 2,2-dialkyl-1,3-propanediols, and cyclohexane dimethylol. In addition, diols that contain other functional groups such as alkyl diethanol amines, diethylene thiols or the like may also be used in some embodiments. Further, in some embodiments, a mono alkyl amine can also be used to directly prepare an alkoxylated diol.

In addition, an amine-terminated derivative of an alkoxylated diol, in some embodiments, comprises a cyanoethylated and reduced polyoxyalkylene glycol, such as a derivative having a long chain ether structure with α and Ω propyl amine groups. Some exemplary amine-terminated derivatives of alkoxylated diols are sold under the trade name JEFFAMINE.

A polymer or oligomer of a hair conditioning composition described herein also comprises at least one hydrophobic block. In some embodiments, a polymer or oligomer comprises a plurality of hydrophobic blocks. A polymer or oligomer, in some embodiments, for example, comprises two hydrophobic blocks. In other embodiments, a polymer or oligomer comprises three hydrophobic blocks or four hydrophobic blocks.

The hydrophobic block or blocks of a polymer or oligomer described herein can constitute any amount of the polymer or oligomer not inconsistent with the objectives of the present invention. In some embodiments, for instance, the hydrophobic blocks are present in the polymer or oligomer in an amount no greater than about 50 weight percent, based on the total weight of the polymer of oligomer. In some embodiments, the hydrophobic blocks are present in the polymer or oligomer in an amount no greater than about 40 weight percent, no greater than about 30 weight percent, no greater than about 20 weight percent, or no greater than about 10 weight percent.

A hydrophobic block of a polymer or oligomer described herein comprises the condensation reaction product of (i) a dicarboxylic acid or dicarboxylic acid equivalent with (ii) a diamine, amino alcohol, diol, or combination thereof. The dicarboxylic acid of a condensation reaction product described herein can comprise any dicarboxylic acid not inconsistent with the objectives of the present invention. In some embodiments, for example, a dicarboxylic acid is aliphatic. In other embodiments, a dicarboxylic acid is aromatic. In some embodiments, a dicarboxylic acid comprises oxalic acid, succinic acid, maleic acid, adipic acid, azelaic acid, sebacic acid, dodecanedioic acid, phthalic acid, isophthalic acid, terephthalic acid, or a combination thereof. Further, a dicarboxylic acid can also comprise one or more additional functional groups, such as an anionic moiety, including a sulfonate moiety. For example, in some embodiments, a dicarboxylic acid comprises a sulfonated isophthalic acid or a sulfonated succinic acid. Moreover, in some embodiments, the dicarboxylic acid is replaced by a dicarboxylic acid equivalent such as an anhydride, acid chloride, or methyl ester of a dicarboxylic acid. A dicarboxylic acid equivalent, in some embodiments, comprises a chemical species that forms the same condensation reaction product as the corresponding dicarboxylic acid forms when reacted with a given reagent such as an diamine, amino alcohol, or diol (except the small molecule produced by the reaction, such as water or methanol, may differ).

Similarly, the diamine of a condensation reaction product described herein can comprise any diamine not inconsistent with the objectives of the present invention. For example, a diamine can comprise primary amino groups, secondary amino groups, or tertiary amino groups. In some embodiments, a diamine comprises an alkylene diamine such as ethylene diamine, 1,2-diaminopropane, 1,3-diaminopropane, 1,4-diaminobutane, 1,6-diaminohexane, or a combination thereof. In some embodiments, a diamine comprises 1,12-diaminododecane. In other embodiments, a diamine comprises a branched chain hexane diamine, such as a DYTEK amine available from Invista. In still other embodiments, a diamine comprises piperazine. Further, in some embodiments, a diamine comprises an N-alkyl diamine or N,N'-dialkyl diamine corresponding to a primary diamine described hereinabove.

The amino alcohol of a condensation reaction product described herein can likewise comprise any amino alcohol not inconsistent with the objectives of the present invention. In some embodiments, an amino alcohol comprises 2-aminoethanol, 1-amino-2-propanol, 1-amino-2-butanol, or a combination thereof. In some embodiments, an amino alcohol comprises an N-alkyl amino alcohol corresponding to a primary amino alcohol described hereinabove.

Similarly, the diol of a condensation reaction product described herein can comprise any diol not inconsistent with the objectives of the present invention. In some embodiments, a diol comprises ethylene glycol, 1,2-propylene glycol, diethylene glycol, dipropylene glycol, triethylene glycol, tripropylene glycol, tetraethylene glycol, 1,3-propanediol, 1,4-butanediol, 1,6-hexanediol, 2-methylpentane-2,4-diol (hexylene glycol), 2,2,4-trimethylpentane-1,3-diol (sold under the trade name TEXANOL), neopentyl glycol or related 2,2-dialkyl-1,3-propanediols, cyclohexane dimethylol, or a combination thereof.

In some embodiments, a hydrophobic block of a polymer or oligomer described herein comprises a polymeric or oligomeric species comprising repeating unit A and at least one repeating unit selected from the group consisting of repeating units B, C, and D:

wherein represents points of attachment in the polymeric or oligomeric chain of the hydrophobic block, $R_1$ and $R_2$ are each independently a linear or branched alkylene group having from 1 to 10 carbon atoms, $R_3$ is a linear or branched alkylene group having from 1 to 16 carbon atoms, a is an integer between 0 and 10, b and c are each independently an integer between 0 and 12, and d is an integer between 0 and 10. For example, in some embodiments, $R_1$, $R_2$ and $R_3$ are methylene ($—CH_2—$). The repeating units can be arranged in the hydrophobic block to provide any type of hydrophobic block not inconsistent with the objectives of the present invention. In some embodiments, for instance, the repeating units are arranged in the hydrophobic block to provide a statistical copolymeric hydrophobic block or a random copolymeric hydrophobic block.

In addition, a polymer or oligomer of a hair conditioning composition described herein can comprise one or more hydrophobic blocks and one or more hydrophilic blocks in any arrangement not inconsistent with the objectives of the present invention. For example, in some embodiments, one or more repeating units are arranged in the polymer or oligomer to provide a statistical copolymeric polymer or oligomer or a random copolymeric polymer or oligomer. In some embodiments, a polymer or oligomer comprises repeating unit A, repeating unit E, and at least one repeating unit selected from the group consisting of repeating units B, C, and D:

wherein represents points of attachment in the polymeric or oligomeric chain of the hydrophobic block, $R_1$ and $R_2$ are each independently a linear or branched alkylene group having from 1 to 10 carbon atoms, $R_3$ is a linear or branched alkylene group having from 1 to 16 carbon atoms, a is an integer between 0 and 10, b and c are each independently an integer between 0 and 12, d is an integer between 0 and 10, and e is an integer between 16 and 64. In some embodiments, $R_1$, $R_2$ and $R_3$ are methylene (—$CH_2$—).

Figure 1:
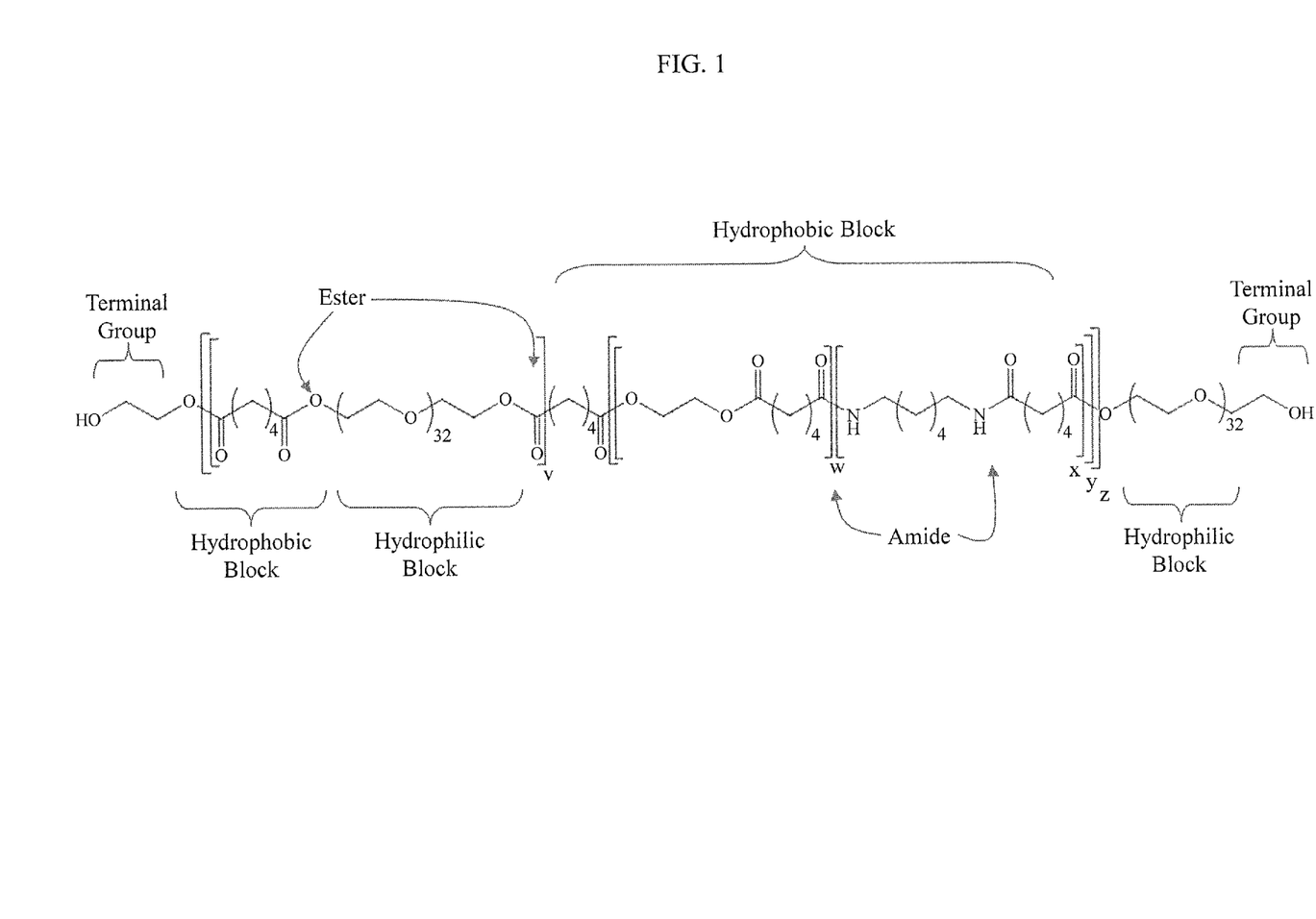
FIG. 1 illustrates a polymer or oligomer of a hair conditioning composition according to one embodiment described herein.

In some embodiments, a polymer or oligomer is a polymer or oligomer of Formula (I):

(I)

wherein a is an integer between 0 and 10, b is an integer between 0 and 12, e is an integer between 16 and 64, v is an integer between 1 and 10, w is an integer between 0 and 10, x is an integer between 0 and 10, y is an integer between 0 and 10, and z is an integer between 1 and 50. In some embodiments, z is an integer between 1 and 40 or between 1 and 20. In the embodiment of FIG. 1, a is 4, b is 4, and e is 32.

Figure 2:
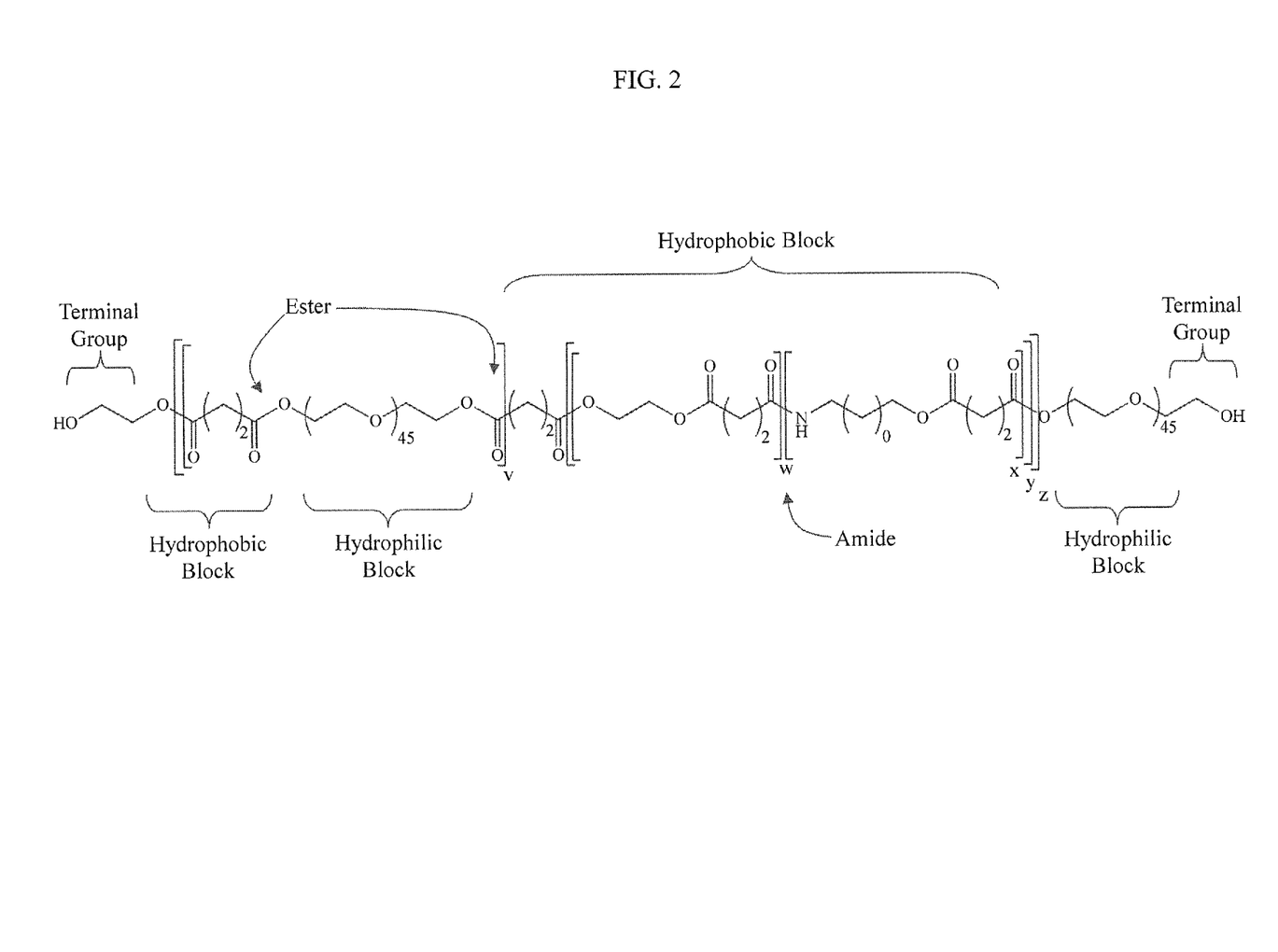
FIG. 2 illustrates a polymer or oligomer of a hair conditioning composition according to one embodiment described herein.

In other embodiments, a polymer or oligomer is a polymer or oligomer of Formula (II):

(II)

wherein a is an integer between 0 and 10, b is an integer between 0 and 12, e is an integer between 16 and 64, v is an integer between 1 and 10, w is an integer between 0 and 10, x is an integer between 0 and 10, y is an integer between 0 and 10, and z is an integer between 1 and 50. In some embodiments, z is an integer between 1 and 40 or between 1 and 20. In the embodiment of FIG. 2, a is 2, b is 0, and e is 45.

A polymer or oligomer of a hair conditioning composition described herein also comprises at least one amide moiety. The amide moiety, in some embodiments, serves as a linkage to connect a hydrophobic block to a hydrophilic block. In other embodiments, the amide moiety does not link a hydrophobic block to a hydrophilic block but instead is within a hydrophobic block or within a hydrophilic block. The presence of at least one amide moiety in a polymer or oligomer described herein, in some embodiments, can provide additional desirable properties to a hair conditioning composition. For example, an amide moiety, in some instances, can facilitate interaction of the polymer or oligomer with hair.

A polymer or oligomer of a hair conditioning composition described herein, in some embodiments, further comprises at least one anionic moiety. In some embodiments, an anionic moiety is part of a hydrophilic block or part of a hydrophobic block. In some embodiments, an anionic moiety is part of a terminal group of the polymer or oligomer. Any anionic moiety not inconsistent with the objectives of the present invention may be used. In some embodiments, for instance, an anionic moiety comprises an oxyanion such as a sulfur oxyanion. In some embodiments, an anionic moiety comprises a sulfite, sulfate, thiosulfate, phosphite, phosphate, nitrite, nitrate, or combination thereof. In some embodiments, an anionic moiety comprises a halide. An anionic group described herein, in some embodiments, can be introduced into a polymer or oligomer described herein by selecting a repeating unit comprising a pendant anionic group, such as a repeating unit comprising a sulfonate. The presence of an anionic group, in some embodiments, can provide improved processability and/or compatibility of a polymer or oligomer with one or more other components of a hair conditioning composition.

Further, a polymer or oligomer of a hair conditioning composition described herein, in some embodiments, is nonionic or neutrally charged. For reference purposes herein, the charge of a polymer or oligomer can refer to the overall charge of the polymer or oligomer. In some embodiments, a polymer or oligomer is anionically charged, including at a pH between about 4 and about 8 or between about 5 and about 7. A neutrally or anionically charged polymer or oligomer, in some embodiments, can provide one or more advantages to a hair conditioning composition, including one or more processing and/or compatibility advantages. In some embodiments, a polymer or oligomer described herein is not cationic and/or does not comprise a cationic moiety such as a quarternary ammonium moiety. Alternatively, in other embodiments, a polymer or oligomer comprises a cationic moiety in the backbone or in a terminal group of the polymer or oligomer.

In addition, in some embodiments, a polymer or oligomer described herein is water dispersible. A water dispersible polymer or oligomer, in some embodiments, is capable of forming a stable colloid in an aqueous medium. In some embodiments, a water dispersible polymer or oligomer does not settle out of an aqueous dispersion when left substantially undisturbed for at least 7 days, at least 14 days, or at least 30 days. Further, for reference purposes herein, a dispersion differs from a solution in which a solvent solvates a solute. Additionally, a polymer or oligomer described herein, in some embodiments, is water dispersible with or without the presence of a surfactant.

Moreover, a polymer or oligomer described herein can have any molecular weight or average molecular weight not inconsistent with the objectives of the present invention. In some embodiments, a polymer or oligomer has weight average molecular weight between about 2000 and about 10,000. In some embodiments, a polymer or oligomer has an average molecular weight between about 2000 and about 8000, between about 2500 and about 7500, between about 2500 and about 5000, or between about 3000 and about 4500.

A polymer or oligomer described herein can be prepared in any manner not inconsistent with the objectives of the present invention. In some embodiments, for instance, a hydrophobic block is prepared through the high temperature condensation of the dicarboxylic acid or dicarboxylic acid equivalent with the selected blend of diamine, amino alcohol, and diol. Further, in some embodiments, one or more hydrophilic blocks are joined to one or more hydrophobic blocks through a condensation reaction to form amide and/or ester linkages. In another embodiment, a polymer or oligomer is prepared by adding a high temperature condensation product to the alkoxylated diol and completing the reaction under normal high temperature esterification conditions. In addition, in some embodiments, one or more of the foregoing condensation reactions is carried out in the presence of a condensation reaction catalyst. Suitable catalysts can include p-toluene sulfonic acid, methane sulfonic acid, a titanium (IV) ester, a zirconium (IV) ester, a tin (II and IV) catalyst, antimony oxide, or another amidation/esterification catalyst known to one of ordinary skill in the art.

A polymer or oligomer described herein can be present in the hair conditioning composition in any amount not inconsistent with the objectives of the present invention. In some embodiments, the polymer or oligomer is present in the composition in an amount between about 0.1 weight percent and about 90 weight percent, based on the total weight of the hair conditioning composition. In some embodiments, the polymer or oligomer is present in the composition in an amount between about 2 weight percent and about 30 weight percent or between about 2 weight percent and about 20 weight percent.

A hair conditioning composition described herein, in some embodiments, further comprises one or more additives. Any additive not inconsistent with the objectives of the present invention may be used. In some embodiments, an additive comprises a thickener, wetting aid, fragrance, or preservative. In some embodiments, an additive comprises one or more of the following: cationic materials such as stearyl trimethyl ammonium chloride; cationic polymers such as a Silicone Quaternium; an ethoxylated alcohol such as POE stearyl alcohol; an amido amine compound such as dimethyl amino propyl amine stearamide; a fatty alcohol such as cetyl or stearyl alcohol; a silicone polymer such as a polyarylated silicone; and an amino polyester. However, in some embodiments, a hair conditioning composition described herein does not comprise such additives. For example, in some embodiments, a hair conditioning composition described herein is silicone-free or substantially silicone-free. A substantially silicone-free composition, in some embodiments, comprises less than about 5 weight percent, less than about 1 weight percent, or less than about 0.5 weight percent silicone.

A composition described herein can be prepared in any manner not inconsistent with the objectives of the present invention. In some embodiments, for example, a composition is prepared by dispersing a polymer or oligomer described herein in water or other aqueous medium to provide an aqueous dispersion of the polymer or oligomer. If an additive is used, preparing can comprise dispersing or dissolving the additive as well. Dispersing or dissolving can be carried out in any manner not inconsistent with the objectives of the present invention, such as by agitation, sonication, and/or heating.

A composition described herein can be used as a hair conditioner. Moreover, a hair conditioning composition described herein can provide one or more desirable properties when applied to hair. For a hair conditioner, relevant properties can include (1) "wet comb," (2) "dry comb," and (3) "static generation."

Wet comb is a measure of the force required to move a comb through a wet tress of hair, where a lower wet comb value indicates superior performance. A wet comb test can be used to indicate the ability of a hair conditioner to lubricate the hair surface. Lubrication of the hair surface can provide manageability of the hair (e.g., resistance to tangles and ease of handing), protection against mechanical damage, and general conditioning. The lubrication performance of a hair conditioner can be measured using an instrumental wet comb test protocol described further hereinbelow.

Dry comb is a measure of the damage done to a tress of hair by repeated combing, where a lower dry comb value indicates superior performance. A dry comb test can be used to indicate the ability of a hair conditioner to provide "boundary lubrication." Boundary lubrication can protect hair against physical damage caused by repeated combing. Boundary lubrication can also reduce breakage of hair fibers. Dry comb can thus be measured by counting broken hair fibers, as described further hereinbelow.

Static generation is a measure of the static charge generated on a tress of hair by repeated combing, where a lower static generation value indicates superior performance. A static generation test can be used to indicate the ability of a hair conditioner to control "fly away" appearance and improve manageability of hair. Untreated hair in low humidity conditions generally has low conductivity, so that static charge generated by combing or other activities is not easily dissipated, possibly causing a "fly away" appearance or poor manageability of hair. Hair conditioners can reduce static charge generation by reducing the amount of static charge that is generated and/or increasing the surface conductivity of the hair. Static generation can be measured as described further hereinbelow.

A hair conditioning composition described herein, in some embodiments, provides a wet comb, dry comb, and/or static generation value when applied to hair superior to those exhibited by untreated hair. In addition, in some embodiments, a hair conditioning composition described herein provides a wet comb, dry comb, and/or static generation value comparable to that provided by silicone-containing compositions. In some embodiments, a hair conditioning composition described herein when applied to hair provides one or more of the following properties:
    (1) Wet comb value of less than about 65 grams (when measured as described herein);
    (2) Dry comb value of less than about 120 broken fibers (when measured as described herein); and
    (3) Static generation of less than about 1400 volts (when measured as described herein).

The wet comb value, in some embodiments, is less than about 60 grams or less than about 50 grams when measured as described herein. The dry comb value, in some embodiments, is less than about 100 broken fibers or less than about 70 broken fibers. In some embodiments, the dry comb value is between about 50 broken fibers and about 70 broken fibers or between about 60 broken fibers and about 65 broken fibers when measured as described herein. The static generation value, in some embodiments, is less than about 1000 volts or less than about 900 volts. In some embodiments, the static generation value is between about 500 volts and about 900 volts or between about 800 volts and about 900 volts when measured as described herein.

In addition to use as a hair conditioner, a composition described herein, in some embodiments, can also be used as a skin care composition, such as a topical lotion or ointment. In some embodiments, a composition described herein can be also be used to treat fibers, including nylon fibers. Treatment of a fiber with a composition described herein, in some embodiments, can increase the hydrophilicity of the fiber or alter the surface of a hydrophobic fiber to become hydrophilic.

Some embodiments described herein are further illustrated in the following non-limiting examples.

Example 1

Hair Conditioning Composition

A hair conditioning composition according to one embodiment described herein is prepared as follows.

A polymer or oligomer is prepared in three stages. First, a "Segment A" is prepared as follows. A three-liter, five-neck resin flask is equipped with a heating mantle, a sub-surface nitrogen inlet, a two level turbine stirrer, a thermocouple-temperature controller, and a condenser-receiver. The fifth neck of the flask is closed with a glass stopper. To the flask is charged 300 grams of adipic acid, 35 grams of sulfonated isophthalic acid (sodium salt), 1475 grams of PEG 1450, and 140 grams of ethylene glycol. The reaction mixture is heated with a nitrogen sparge to 170° C., and 1.0 grams of tetrabutoxy zirconate is added to the reaction mixture. The temperature of the reaction mixture is then increased to 230° C. over a period of 4 to 5 hours. At that point, the sparge is increased and the acid value is monitored. The reaction is considered complete when the acid value reaches 2.5. The reaction mixture is then cooled to 150° C. and held for further reaction.

A "Segment B" is prepared as follows. A 1-liter high pressure autoclave reactor is equipped with a heating mantle, an anchor stirrer, a sub-surface nitrogen inlet, a pressure release valve, a blow out port, a valve outlet connected to a condenser-receiver, and a bottom outlet. To the autoclave reactor is charged 105 grams of adipic acid, 125 grams of ethylene glycol, and 375 grams of 1.0 to 1.0 adipic acid salt of hexamethylene diamine. The reactor is purged with nitrogen and heated with all valves closed. The temperature is raised to 260° C. (pressure of 18 bar) and held at this temperature/pressure for 2 hours. The pressure in the reactor is then slowly reduced to atmospheric pressure through the condensing system, and the temperature is then reduced to 250° C. The mixture is then held at this temperature and slowly sparged with nitrogen for two hours. At this point, the reactor contains about 515 grams of ester amide with an acid value of 10.5.

Next, Segments A and B are combined to complete the preparation. A heated line is run from the bottom outlet of the autoclave reactor to the fifth neck of the 3-liter resin flask containing Segment A. Segment A, in the 3 liter resin flask, is heated to 240° C. and the autoclave reactor is pressurized with nitrogen to 2 bar. The bottom outlet is partially opened and the contents of the autoclave reactor, Segment B, are added to Segment A over a one hour period. During the addition, the temperature is held at 240-250° C. Upon completion of the addition, the nitrogen sparge is increased and the acid value monitored. In one hour, the acid value is reduced to less than 1.5 and vacuum is applied (200 mm) to the flask to assist in the removal of ethylene glycol and to build the molecular weight of the polymer or oligomer (as monitored by the viscosity of the reaction product). In 45 minutes, the viscosity reaches 2.7 poise (at 200° C., measured with a cone and plate rheometer). The vacuum is then released, and the reaction mixture is cooled to 205° C.

The product is a light yellow polymer or oligomer with an acid value of 0.8, a hydroxyl value of 42, and a viscosity of 2.95 poise (at 200° C., measured with a cone and plate rheometer).

The majority of the product is discharged into a stirred, 18-liter bucket containing 8 liters of 60° C. deionized water. During the addition, the water temperature rises to about 80° C., and the mixture, which is initially two phases, on cooling becomes one phase at approximately 40° C. The solids in the solution are checked and adjusted to provide a 20% aqueous dispersion of the polymer/oligomer.

Example 2

Hair Conditioning Performance

The hair conditioning performance of the composition of Example 1 was evaluated as follows.

Evaluation was carried out according to standard hair conditioning test protocols for determining wet comb, dry comb, and static generation values developed by TRI Princeton (Princeton, N.J.). Tests were conducted using European Medium Brown hair (International Hair Importers & Products, Glendale, N.Y.). The hair was divided into 3-gram tresses, 8 inches in length. Prior to testing, the tresses to be used in the wet comb and dry comb tests were chemically damaged using a hydrogen peroxide treatment. Specifically, for wet comb tests, the tresses were bleached using a 6% hydrogen peroxide solution at a pH of 10.2. The tresses were left in contact with the bleach solution for 40 minutes at 40° C. The tresses were then thoroughly rinsed with water at 40° C. at a flow rate of 1.0 gallon per minute (GPM). For dry comb tests, tresses were bleached using a 9% hydrogen peroxide solution at a pH of 10.2. The tresses were left in contact with the bleach solution for 20 minutes at 40° C. The tresses were then thoroughly rinsed with water at 40° C. at a flow rate of 1.0 GPM. The process was then repeated three times for the dry comb tests to provide significantly damaged hair. The hair used in the static generation tests was used as received.

For each test, the composition of Example 1 was diluted to give a 3% aqueous dispersion. This dispersion was applied to 8 to 10 tresses at a dosage rate of 15% v/w of the tress weight (equivalent to 0.45 mL of aqueous dispersion per tress) and was left on the hair for 30 seconds prior to rinsing for 30 seconds (1.0 GPM water flow at 40° C.). In addition, for each protocol, the tests were run against 8 to 10 untreated tresses of the same type. The results were also compared against the following standard hair conditioning treatments:

(1) "High Silicone" treatment designed to deposit 600 ppm of a silicone on the hair;

(2) "Moderate Silicone" treatment designed to deposit 150 ppm of a silicone on the hair; and (3) "Silicone Free" treatment based on a blend of cationic and nonionic conditioning agents not in accordance with the present invention.

Figure 3:
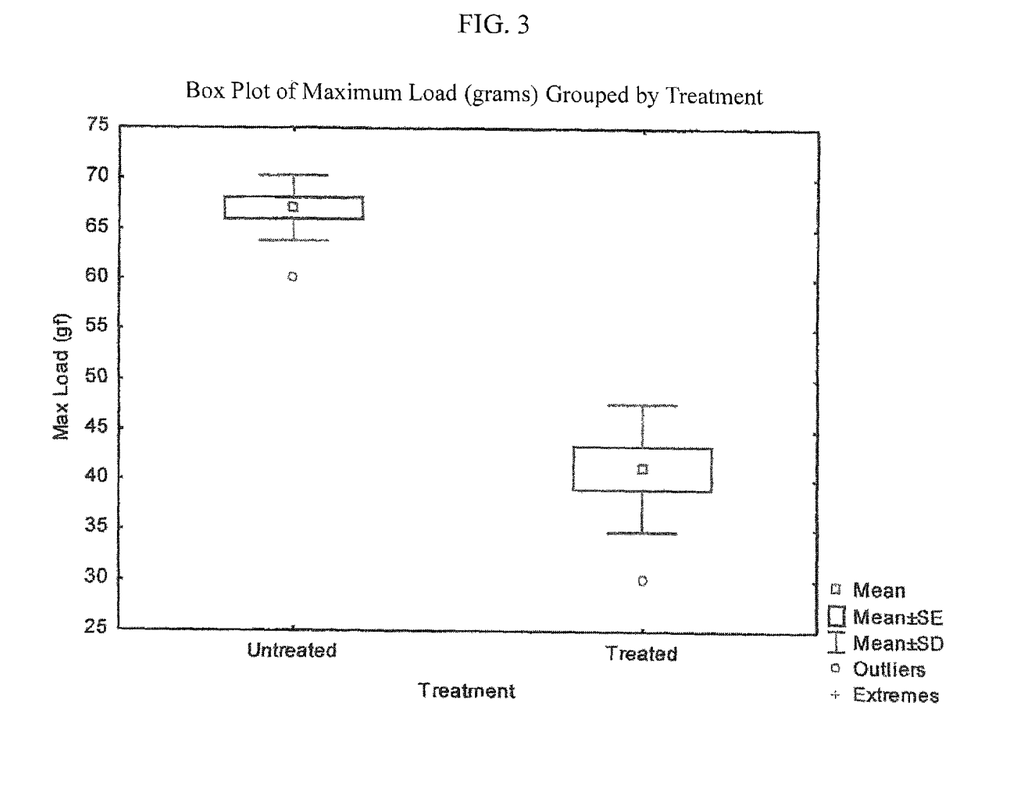
FIG. 3 illustrates the hair conditioning performance of a hair conditioning composition according to one embodiment described herein.

The wet comb test was carried out using the general method of Garcia and Diaz (JSCC 27: 379-398, 1976). A hair tress was suspended from the load cell of an Instron Tensile Tester and pulled through a comb. The frictional force was measured by a load cell. The wet comb force on individual tresses was measured until six repeated stroked registered constant results. Tests were carried out on 8 treated tresses and 8 untreated tresses. The results are given in Table 1 and presented graphically in FIG. 3. Statistical analysis was performed using a student's t-test at 95% confidence level. The difference in results for untreated and treated tresses was statistically significant.

TABLE 1

Wet Comb Results

| Treatment | Number | Mean (grams) | Std Dev | Std Err Mean |
| --- | --- | --- | --- | --- |
| Untreated | 8 | 67.0 | 3.2 | 1.1 |
| Treated | 8 | 41.2 | 6.4 | 2.3 |

The treatment of hair tresses with a 3% dispersion of the composition of Example 1 was observed to provide a significant reduction in the wet comb force relative to the untreated control. Comparisons of the performance of the composition of Example 1 versus standard hair conditioning treatments are given in Table 4.

Figure 4:
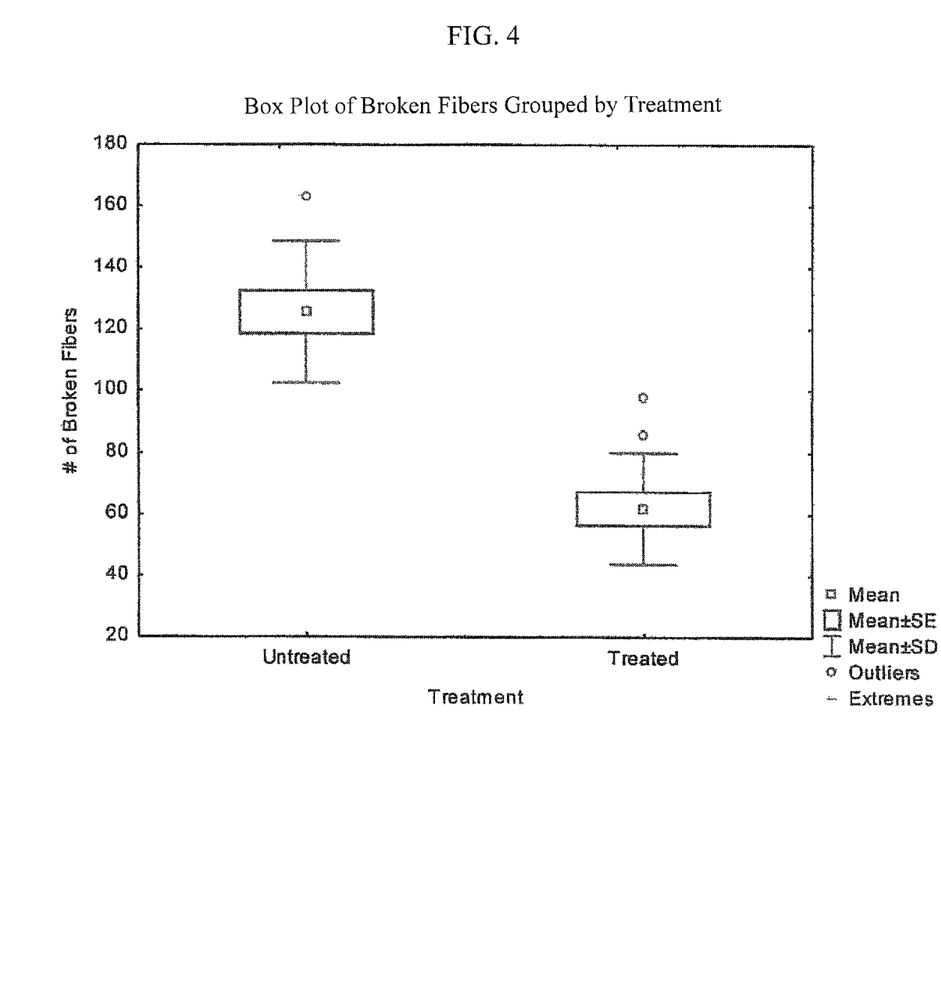
FIG. 4 illustrates the hair conditioning performance of a hair conditioning composition according to one embodiment described herein.

The dry comb test was carried out using an automated combing device (TRI) including a hollow rotating drum-like assembly and four combs mounted at 90 degree angles so that one complete drum revolution to combs a tress four times. Tresses were repeatedly combed (10,000 total strokes), and any broken fiber fragments were collected for counting every 1000 strokes. The tresses (10 treated tresses and 10 untreated tresses) were combed at 25° C. and 60% relative humidity (RH). The results are given in Table 2 and presented graphically in FIG. 4. Statistical analysis was performed using a student's t-test at 95% confidence level. The difference in results for untreated and treated tresses was statistically significant.

TABLE 2

Dry Comb Results

| Treatment | Number | Mean (# broken fibers) | Std Dev | Std Err Mean |
| --- | --- | --- | --- | --- |
| Untreated | 10 | 125 | 23 | 7.3 |
| Treated | 10 | 41 | 18 | 5.7 |

The treatment of hair tresses with a 3% dispersion of the composition of Example 1 was observed to provide a significant reduction in the number of broken fibers relative to the untreated control. Comparisons of the performance of the composition of Example 1 versus standard hair conditioning treatments are given in Table 4.

Figure 5:
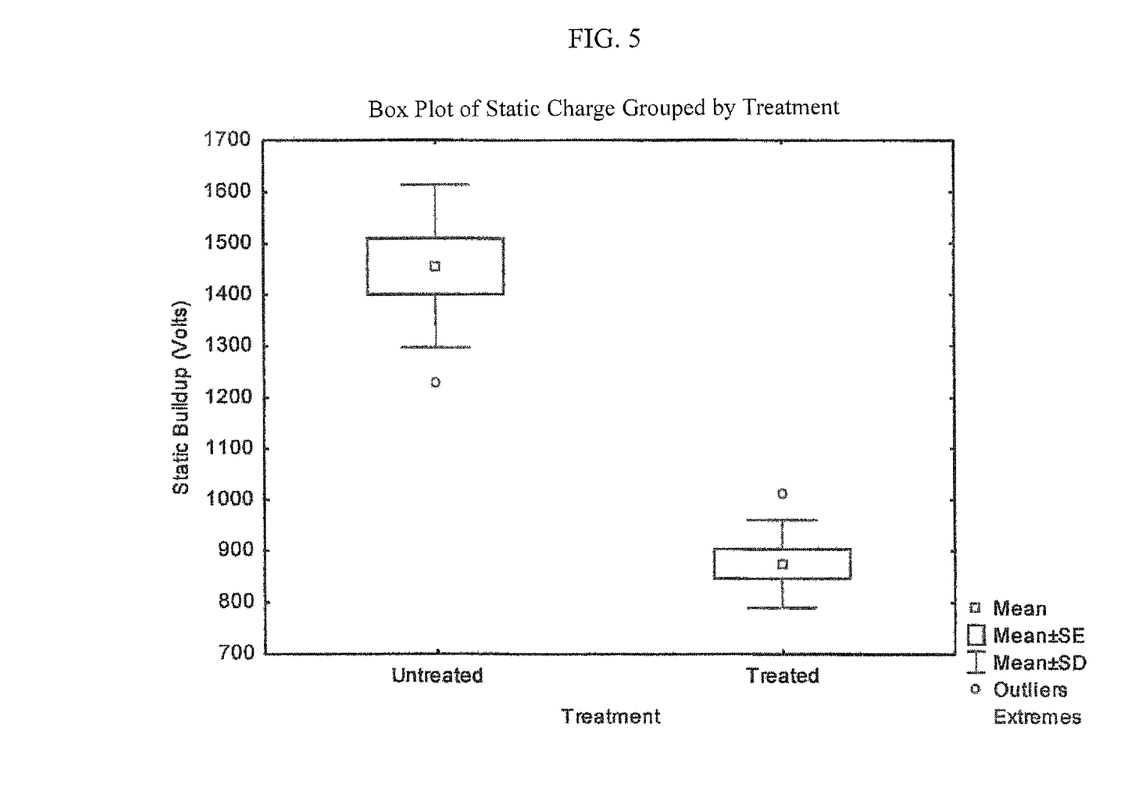
FIG. 5 illustrates the hair conditioning performance of a hair conditioning composition according to one embodiment described herein.

The static generation test was carried out based on the method of Lunn and Evans (JSCC, 28: 549-569, 1977). Eight treated and 8 untreated hair tresses were equilibrated under controlled temperature and humidity conditions (25° C. and 30% RH) and then brushed with an automated brushing device (TRI) while monitoring the build-up of static charge on the hair. The results are given in Table 3 and presented graphically in FIG. 5. Statistical analysis was performed using a student's t-test at 95% confidence level. The difference in results for untreated and treated tresses was statistically significant.

TABLE 3

Static Generation Results

| Treatment | Number | Mean (volts) | Std Dev | Std Err Mean |
| --- | --- | --- | --- | --- |
| Untreated | 8 | 1455 | 158 | 56.0 |
| Treated | 8 | 875 | 85.2 | 30.1 |

The treatment of hair tresses with a 3% dispersion of the composition of Example 1 was observed to provide a significant reduction in the amount of static charge generated during brushing relative to the untreated control. Comparisons of the performance of the composition of Example 1 versus standard hair conditioning treatments are given in Table 4.

TABLE 4

Comparative Results

| Treatment | Wet Comb (grams) | Dry Comb (# broken fibers) | Static Charge (volts) |
| --- | --- | --- | --- |
| Untreated | 67 | 125 | 1450 |
| Composition of Example 1 | 41 | 62 | 875 |
| High Silicone | 35-40 | 30-45 | 400-500 |
| Mid Silicone | 40-50 | 50-70 | 800-1100 |
| Silicone Free | 50-60 | 70-100 | 200-500 |

Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. A hair conditioning composition comprising a polymer or oligomer comprising:
   at least one hydrophilic block comprising an alkoxylated diol or amine-terminated derivative thereof; and
   at least one hydrophobic block comprising a condensation reaction product of (i) a dicarboxylic acid or dicarboxylic acid equivalent and (ii) a diamine, amino alcohol, diol, or combination thereof,
wherein the hydrophilic block and the hydrophobic block are bonded together through an amide or ester linkage and the polymer or oligomer comprises at least one amide moiety, and
wherein the at least one hydrophobic block comprises a polymeric or oligomeric species comprising repeating unit A and at least one repeating unit selected from the group consisting of repeating units B, C, and D:

(A)

-continued wherein

{ represents points of attachment in the polymeric or oligomeric chain of the hydrophobic block, $R_1$ and $R_2$ are each independently a linear or branched alkylene group having from 1 to 10 carbon atoms, $R_3$ is a linear or branched alkylene group having from 1 to 16 carbon atoms, a is an integer between 0 and 10, b and c are each independently an integer between 0 and 12, and d is an integer between 2 and 10.

2. The composition of claim 1, wherein the polymer or oligomer comprises a plurality of hydrophilic blocks connected by one or more hydrophobic blocks.

3. The composition of claim 1, wherein the at least one hydrophilic block comprises a poly(ethylene glycol).

4. The composition of claim 1, wherein the at least one hydrophilic block has a molecular weight of at least about 1000.

5. The composition of claim 1, wherein the at least one hydrophilic block is present in the polymer or oligomer in an amount of about 50 weight percent to about 90 weight percent.

6. The composition of claim 1, wherein the repeating units are arranged in the hydrophobic block to provide a statistical copolymeric hydrophobic block or a random copolymeric hydrophobic block.

7. The composition of claim 1, wherein the at least one hydrophobic block is present in the polymer or oligomer in an amount no greater than about 50 weight percent.

8. A hair conditioning composition comprising a polymer or oligomer comprising:
  at least one hydrophilic block comprising an alkoxylated diol or amine-terminated derivative thereof; and
  at least one hydrophobic block comprising a condensation reaction product of (i) a dicarboxylic acid or carboxylic acid equivalent and (ii) a diamine, amino alcohol, diol, or combination thereof,
wherein the hydrophilic block and the hydrophobic block are bonded together through an amide or ester linkage and the polymer or oligomer comprises at least one amide moiety, and
wherein the polymer or oligomer comprises repeating unit A, repeating unit E, and at least one repeating unit selected from the group consisting of repeating units B, C, and D:

wherein

{ represents points of attachment in the polymeric or oligomeric chain of the hydrophobic block, $R_1$ and $R_2$ are each independently a linear or branched alkylene group having from 1 to 10 carbon atoms, $R_3$ is a linear or branched alkylene group having from 1 to 16 carbon atoms, a is an integer between 0 and 10, b and c are each independently an integer between 0 and 12, d is an integer between 2 and 10, and e is an integer between 16 and 64.

9. The composition of claim 8, wherein the repeating units are arranged in the polymer or oligomer to provide a statistical copolymeric polymer or oligomer or a random copolymeric polymer or oligomer.

10. A hair conditioning composition comprising a polymer or oligomer comprising:
  at least one hydrophilic block comprising an alkoxylated diol or amine-terminated derivative thereof; and
  at least one hydrophobic block comprising a condensation reaction product of (i) a dicarboxylic acid or carboxylic acid equivalent and (ii) a diamine, amino alcohol, diol, or combination thereof,
wherein the hydrophilic block and the hydrophobic block are bonded together through an amide or ester linkage and the polymer or oligomer comprises at least one amide moiety, and wherein the polymer or oligomer is a polymer or oligomer of Formula (I):

wherein a is an integer between 0 and 10, b is an integer between 0 and 12, e is an integer between 16 and 64, v is an integer between 1 and 10, w is an integer between 0 and 10, x is an integer between 1 and 10, y is an integer between 1 and 10, and z is an integer between 1 and 50, or the polymer or oligomer is a polymer or oligomer of Formula (II):

wherein a is an integer between 0 and 10, b is an integer between 0 and 12, e is an integer between 16 and 64, v is an integer between 1 and 10, w is an integer between 0 and 10, x is an integer between 1 and 10, y is an integer between 1 and 10, and z is an integer between 1 and 50.

11. The composition of claim 10, wherein the polymer or oligomer is a polymer or oligomer of Formula (I).

12. The composition of claim 1, wherein the polymer or oligomer has a molecular weight between about 2000 and about 4500.

13. An aqueous dispersion comprising the composition of claim 12.

14. The composition of claim 10, wherein the polymer or oligomer is a polymer or oligomer of Formula (II).

15. An aqueous dispersion comprising the composition of claim 8, wherein the polymer or oligomer has a molecular weight between about 2000 and 4500.

16. An aqueous dispersion comprising the composition of claim 10, wherein the polymer or oligomer has a molecular weight between 2000 and 4500.

17. A method for conditioning hair, comprising, applying the composition of claim 1 to hair.

18. A method for conditioning hair, comprising, applying the composition of claim 8 to hair.

19. A method for conditioning hair, comprising, applying the composition of claim 11 to hair.

20. A method for conditioning hair, comprising, applying the composition of claim 14 to hair.

* * * * *